(12) United States Patent
Morgenstern Lopez et al.

(10) Patent No.: US 11,660,204 B2
(45) Date of Patent: May 30, 2023

(54) METHOD FOR INSTANT LUMBAR SPINE FUSION

(71) Applicant: ENDOSPINE, S.L., Sant Pere del Tarter (AD)

(72) Inventors: Rudolf Morgenstern Lopez, Esplugues de Llobregat (ES); Christian Rudolf Morgenstern De Muller, Esplugues de Llobregat (ES)

(73) Assignee: ENDOSPINE, S.L., Sant Pere Del Tarter (AD)

( * ) Notice: Subject to any disclaimer, the term of this patent is extended or adjusted under 35 U.S.C. 154(b) by 534 days.

(21) Appl. No.: 16/896,686

(22) Filed: Jun. 9, 2020

(65) Prior Publication Data

US 2021/0378837 A1 Dec. 9, 2021

(51) Int. Cl.
| | |
|---|---|
| *A61F 2/44* | (2006.01) |
| *A61L 27/36* | (2006.01) |
| *A61L 27/12* | (2006.01) |
| *A61L 27/16* | (2006.01) |
| *A61L 27/18* | (2006.01) |
| *A61L 27/54* | (2006.01) |
| *A61L 27/38* | (2006.01) |
| *A61F 2/46* | (2006.01) |
| *A61B 90/00* | (2016.01) |

(52) U.S. Cl.
CPC .......... *A61F 2/4455* (2013.01); *A61F 2/4611* (2013.01); *A61L 27/12* (2013.01); *A61L 27/16* (2013.01); *A61L 27/18* (2013.01); *A61L 27/365* (2013.01); *A61L 27/3608* (2013.01); *A61L 27/3616* (2013.01); *A61L 27/3821* (2013.01); *A61L 27/3847* (2013.01); *A61L 27/54* (2013.01); *A61B 2090/376* (2016.02); *A61F 2002/448* (2013.01); *A61L 2300/412* (2013.01); *A61L 2300/414* (2013.01); *A61L 2430/02* (2013.01); *A61L 2430/38* (2013.01)

(58) Field of Classification Search
CPC ......... A61F 2/4611; A61F 2/44; A61L 27/365
See application file for complete search history.

(56) References Cited

U.S. PATENT DOCUMENTS

2020/0008944 A1\* 1/2020 Morgenstern Lopez .................... A61F 2/28

\* cited by examiner

*Primary Examiner* — Jason-Dennis N Stewart
(74) *Attorney, Agent, or Firm* — Knobbe, Martens, Olson & Bear, LLP

(57) ABSTRACT

A method for instant lumbar spine fusion between two vertebrae in a patient includes establishing under X-ray fluoroscopy the location of the transpedicular notch of the next lower vertebra in caudal direction, making a percutaneous incision to the transpedicular notch, inserting a cannulated guide, drilling a transpedicular approach from the pedicle of the lower vertebra to the anterior part of the vertebral body of the vertebrae above the disc to be treated, inserting a working cannula through the previously drilled approach reaching the intervertebral disk, cleaning and scrapping the intervertebral disk space, inserting transpedicularly at least one intervertebral stabilizing screw, and acting on both intervertebral screws with screwdrivers in order to distract or contract both screws allowing to adjust or correct the intervertebral distance of the disk. The method can be performed on an outpatient basis.

15 Claims, 12 Drawing Sheets

METHOD FOR INSTANT LUMBAR SPINE FUSION

BACKGROUND

Field

The present disclosure is related to the field of biomedicine, in particular, to a method for instant lumbar spine fusion between two vertebrae.

Description of the Related Art

The spine is made up of small bones, called vertebrae. The vertebrae protect and support the spinal cord. The upper and lower surfaces of the vertebra body give attachment to the intervertebral discs. The posterior part of a vertebra forms a vertebral arch, in eleven parts, consisting of two pedicles, two laminae, and seven processes. The laminae give attachment to the ligamenta flava (ligaments of the spine). There are vertebral notches formed from the shape of the pedicles, which form the intervertebral foramina when the vertebrae articulate. These foramina are the entry and exit conducts for the spinal nerves. The body of the vertebra and the vertebral arch form the vertebral foramen, the larger, central opening that accommodates the spinal canal, which encloses and protects the spinal cord.

Between each vertebra there is an intervertebral disc. These flat, round cushions act like shock absorbers by helping absorb pressure and keep the bones from rubbing against each other. The intervertebral disc also binds adjacent vertebrae together. The intervertebral discs are a type of joint in the spine. Intervertebral disc joints can bend and rotate a bit but do not slide as do most body joints.

Each vertebra has two other sets of joints, called facet joints. The facet joints are located at the back of the spine (posterior). There is one facet joint on each lateral side (right and left). One pair of facet joints faces upward (called the superior articular facet) and the other pair of facet joints faces downward (called the inferior articular facet). The inferior and superior facet joints mate, allowing motion (articulation), and link vertebrae together. Facet joints are positioned at each level to provide the needed limits to motion, especially to rotation and to prevent forward slipping (spondylolisthesis) of that vertebra over the one below.

Degenerative changes in the spine can adversely affect the ability of each spinal segment to bear weight, accommodate movement, and provide support. When one segment deteriorates to the point of instability, it can lead to localized pain and difficulties. Segmental instability allows too much movement between two vertebrae. The excess movement of the vertebrae can cause pinching or irritation of nerve roots. It can also cause too much pressure on the facet joints, leading to inflammation. It can cause muscle spasms as the paraspinal muscles try to stop the spinal segment from moving too much. The instability eventually results in faster degeneration in this area of the spine A fusion is an operation where two bones, usually separated by a joint, are allowed to grow together into one bone. The medical term for this type of fusion procedure is arthrodesis.

Lumbar spinal fusion has been performed for decades. There are several different techniques that may be used to fuse the spine. There are also different "approaches" a surgeon can take to reach a spine. Lumbar fusion procedures have been used in the treatment of pain and the effects of degenerative changes in the lower back. Most individuals have five lumbar vertebrae, while some have four or six. Lumbar disorders that normally affect L5 will affect L4 or L6 in these latter individuals. A lumbar fusion is a fusion in the lumbar region in the spine.

Current spinal fusions use some type of natural or artificial bone material, called a bone graft, to help promote the fusion. Generally, small pieces of bone are placed into the space between the vertebrae to be fused.

A bone graft is primarily used to stimulate bone healing. It increases bone production and helps the vertebrae heal together into a solid bone. Sometimes larger, solid pieces are used to provide immediate structural support to the vertebrae.

In the past, a bone graft harvested from the patient's pelvis was the only option for increasing the material needed for fusing the vertebrae. This type of graft is called an autograft. Harvesting a bone graft requires an additional incision during the operation. It lengthens surgery and can cause increased pain after the operation.

Nowadays, several artificial bone graft materials have also been developed, such as demineralized bone matrices (DBMs), bone morphogenetic proteins (BMPs) or synthetic bone.

One way of achieving a lumbar fusion is a procedure called anterior lumbar interbody fusion (ALIF). In this procedure, the surgeon works on the spine from the front (anterior) and removes a spinal disc in the lower (lumbar) spine. The surgeon inserts a bone graft into the space between the two vertebrae where the disc was removed (the interbody space). The goal of the procedure is to stimulate the vertebrae to grow together into one solid bone (known as fusion). Fusion creates a rigid and immovable column of bone in the problem section of the spine. This type of procedure is used to try and reduce back pain and other symptoms.

Currently, these procedures entail invasive open surgical techniques. Further, ALIF entails the surgical removal of the disc. Like all invasive open surgical procedures, such operations on the spine risk infections and require hospitalization. Invasive open surgical techniques involving the spine continue to be a challenging and difficult area.

SUMMARY

In a first aspect, the present disclosure refers to a method for instant lumbar spine fusion between two vertebrae in a patient in need thereof comprising:
  a) establishing under X-ray fluoroscopy the location of the transpedicular notch of the next lower vertebra in caudal direction;
  b) making a percutaneous incision of about 5-10 mm approximately 5 cm off of midland caudal to said transpedicular notch;
  c) inserting a cannulated guide following an anteroposterior (AP) trajectory of C between 18° and 25° and in a lateral trajectory of A or B between 35° and 50°;
  d) drilling a transpedicular approach from the pedicle of the lower vertebra to the anterior part of the vertebral body of the vertebrae above the disc to be treated;
  e) inserting a working cannula through the previously drilled approach reaching the intervertebral disk;
  f) cleaning and scrapping the intervertebral disk space;
  g) inserting transpedicularly at least one intervertebral stabilizing screw, said screw comprising two threads each to be threaded to contiguous vertebrae, wherein the distal thread is threaded to the upper vertebra penetrating about 5-10 mm into the body of said upper vertebra and the proximal thread is threaded inside the pedicle and the body of the lower vertebra;

h) acting on both intervertebral screws with screwdrivers in order to distract or contract both screws allowing to adjust or correct the intervertebral distance of the disk;

In this aspect, the method is performed on an outpatient basis using local anesthesia and each of steps (b) through (h) is followed by active or real-time fluoroscopy.

In some embodiments, the percutaneous incision of is of about 8 mm.

In some embodiments, after step h), the method further comprises introducing a bone remodeling composition in the void created in the disk space said composition promoting bone formation.

In some embodiments, the patient in need thereof is a patient requiring fusion to treat pseudoarthrosis (unsuccessful previous fusion) spinal stenosis, spondylolisthesis (Grade 1 or 2 if single-level; Grade 1 if two-level), or degenerative disc disease as defined as back pain of discogenic origin with degeneration of the disc confirmed by history and radiographic studies.

In some embodiments, a series of Nitinol Disc Cutters, varying in length and shape, are used to prepare the disc space to accommodate various anatomies or surgical situations.

In some embodiments, the bone remodeling composition comprises autogenous bone and allogenic demineralized bone matrix (DBM) mixed with autologous blood mixed with calcium phosphate.

In some embodiments, the bone remodeling composition comprises at least one of the following elements, poly (methyl methacrylate) (PMMA), bisphenol A-glycidyl methacrylate (bis-GMA) and poly(lactic-co-glycolic acid) (PLGA).

In some embodiments, the bone remodeling composition comprises at least PMMA and/or PLGA.

In some embodiments, the calcium phosphate provider is hydroxyapatite, brushite or tricalcium phosphate.

In some embodiments, the calcium phosphate provider is hydroxyapatite.

In some embodiments, the bone remodeling composition comprises osteogenic factors selected from whole blood, blood-derived growth factors and osteogenic stem cells.

In some embodiments, the osteogenic factors are blood-derived growth factors.

In some embodiments, the volume of the bone remodeling composition is between 7 cc and 10 cc.

In some embodiments, the external diameter of the proximal thread of the intervertebral stabilizing screw is greater than the diameter of the distal thread.

In some embodiments, the intervertebral stabilizing screw comprises at least two fill holes.

DETAILED DESCRIPTION

Spinal fusion is surgery to permanently connect two or more vertebrae in the spine, eliminating motion between them. Currently, there are several methods of lumbar spine fusion.

The inventors of the present application have developed a new method for instant lumbar spine fusion between two vertebrae using a double screw system (DSS) which includes surgical instruments for creating a safe and reproducible posterior transpedicular access route to the T10-L5 vertebral bodies.

The DSS technique used in the method of an embodiment of the present disclosure features instrumentation to enable standard of care fusion principles, distraction, and stabilization of the anterior lumbar column while mitigating the soft tissue trauma associated with traditional lumbar fusion through open surgical incisions.

Using DSS, the lumbar spine is accessed through a transpedicular channel on the posterior face of the dorsal or lumbar vertebrae. This atraumatic tissue plane alleviates the need for the surgeon to cut through supporting muscles and ligaments, thus reducing postoperative pain and the prospect of complications. The method of this embodiment of the present disclosure can be performed in an outpatient basis using a local anesthesia and each of the steps can be followed by active or real-time fluoroscopy.

Surprisingly, the inventors found that using the method of an embodiment of the present disclosure the lumbar spine is accessed through a transpedicular channel on the posterior face of the dorsal or lumbar vertebrae. This atraumatic tissue plane alleviates the need for the surgeon to cut through supporting muscles and ligaments, thus reducing postoperative pain and the prospect of complications. Therefore, the method can be carried out immediately using percutaneous techniques, local anesthesia and outpatient surgical centers.

Trajectory can be extremely important in the method of some embodiments of the present disclosure. Radiographic images, including a full dorsal or lumbar view, can be used to determine if the anatomy is suitable. Magnetic resonance imaging (MRI) is preferred in order to best visualize soft tissue anatomy. The standard field of view for dorsal and lumbar MRI and computed tomography (CT) must be used to aid in pre-operative planning. Therefore, the first step is establishing under X-ray fluoroscopy the location of the transpedicular notch of the next lower vertebra in caudal direction.

Figure 1:
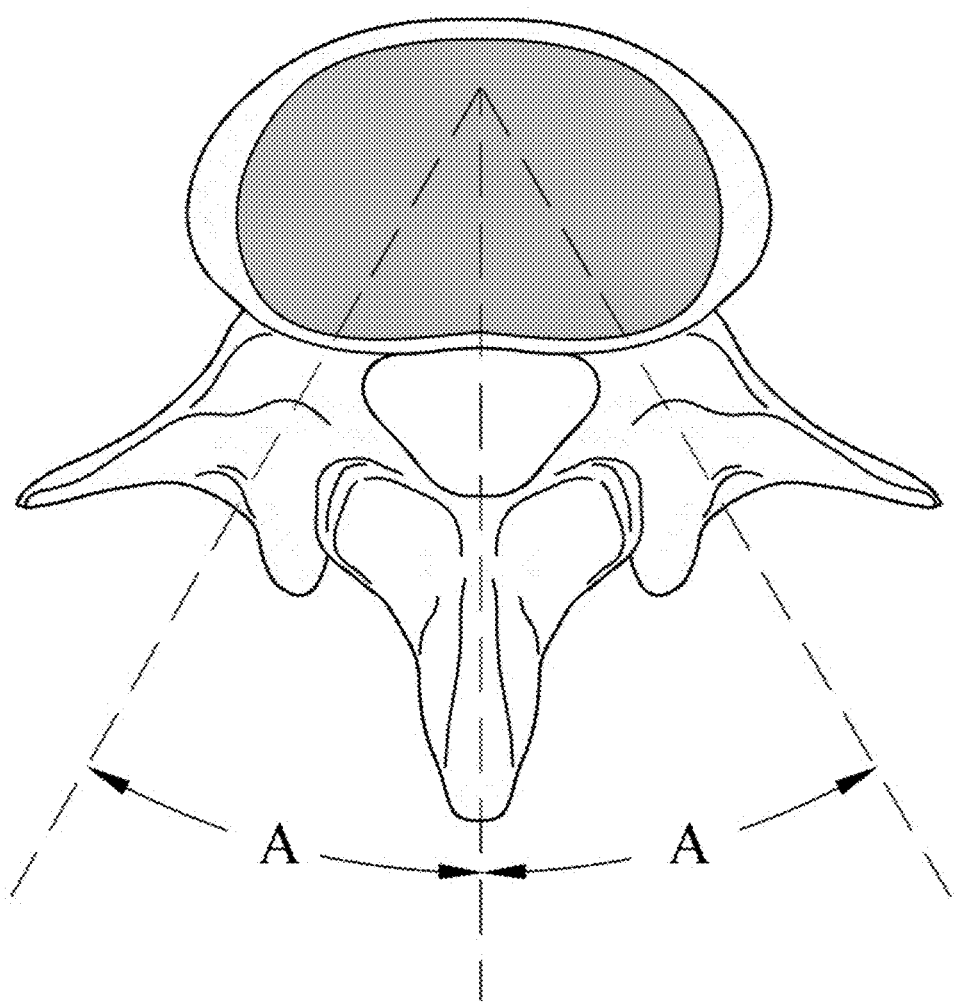
FIG. 1 is a view from a sagittal plane of the vertebral level that will be fused. The figure shows the lower vertebra and the disk space, the upper vertebra having been omitted. The trajectory of introduction of the screw according to an embodiment of the present disclosure has also been shown.
Figure 4:
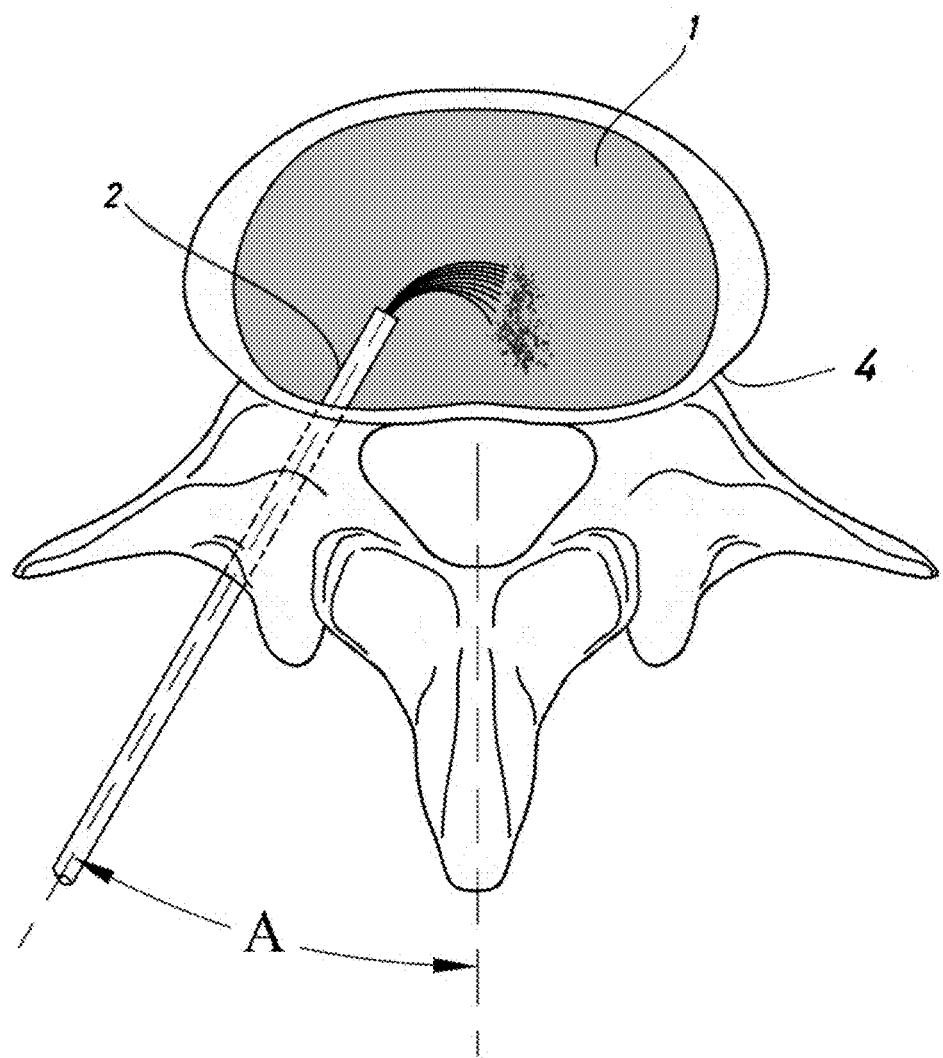
FIG. 4 shows a first phase of an example of the process of putting in place the device according to an embodiment of the present disclosure, in which the disk content (nucleus) has been omitted.
Figure 6:
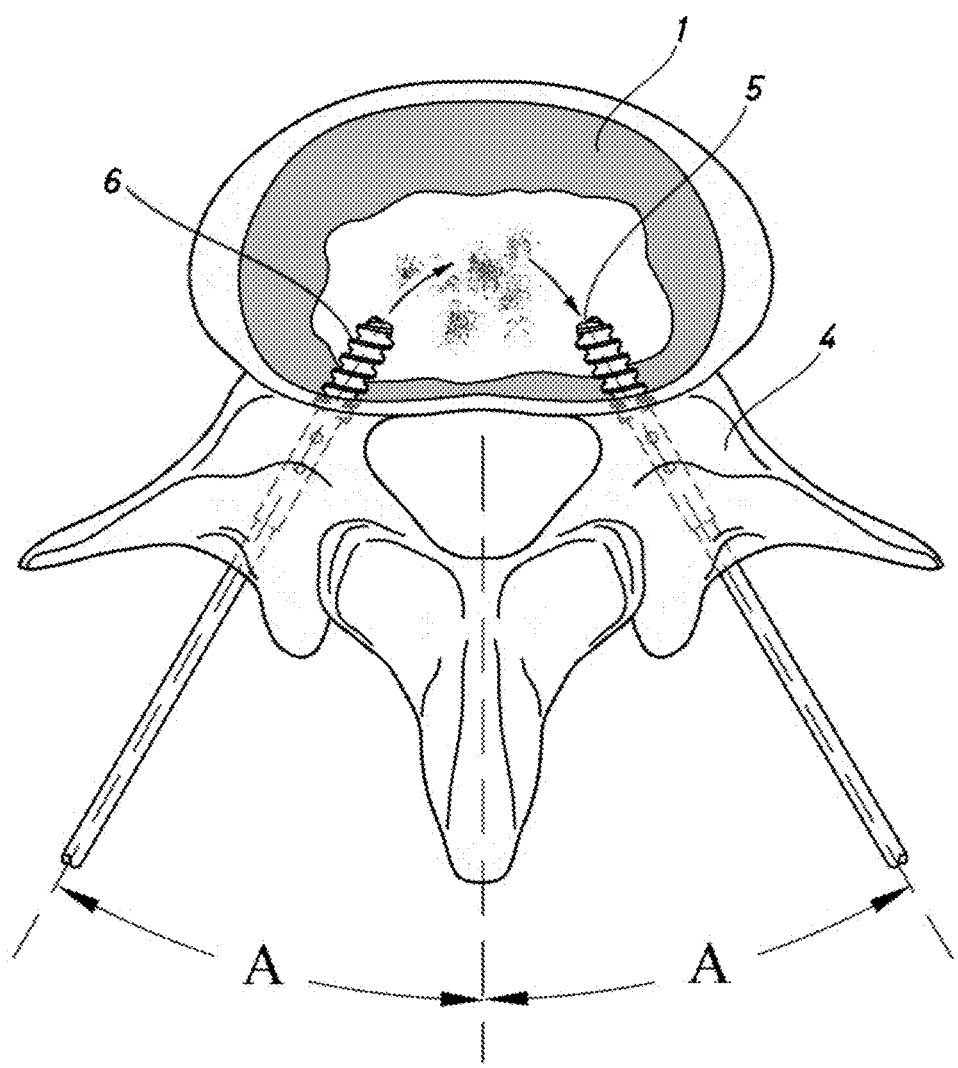
FIG. 6 shows diagrammatically a third phase of the device placement process.

After visualization, the method of some embodiments of the present disclosure involves making a percutaneous incision of about 5-10 mm approximately 5 cm off of midland caudal to said transpedicular notch and inserting a cannulated guide following an antero-posterior (AP) trajectory of C between 18° and 25°, as shown in FIG. 6 and in a lateral trajectory of A or B between 35° and 50°, as shown in FIGS. 1 and 4.

The method of some embodiments of the present disclosure uses titanium alloy implant that utilizes a differential thread pitch to attain distraction of the disc space during implant insertion. These implants have several advantages such as restores disc height via distraction, indirectly decompresses the neural foramen and allows an instantaneous rigid fixation of the selected dorsal or lumbar segment.

This technique also allows for fine trajectory adjustments of the Guide Pin on the vertebrae and may reduce any interference from associated soft tissues at the incision site.

In one embodiment, the Blunt Dissecting Tool to penetrate the fascia immediately below the ligaments is used.

In one embodiment, a dissecting tool along the midline, is used for keeping the tip engaged on the anterior cortex of the vertebrae while continue to check the A/P and lateral fluoroscopic views. This maneuver is accomplished with "fingertip" control and should be completed using fluoroscopic guidance in both A/P and lateral planes.

Once the trajectory is established, the Blunt Stylet for the Beveled Guide Pin is exchanged, ensuring the tip of the bevel is aligned with the thumbscrew on the handle.

Next step of the present embodiment of the method is drilling a transpedicular approach from the pedicle of the lower vertebra to the anterior part of the vertebral body of the vertebrae above the disc to be treated, and inserting a working cannula through the previously drilled approach reaching the intervertebral disk.

It is important to clean and scrap the intervertebral disk space before inserting transpedicularly at least one intervertebral stabilizing screw, said screw comprising two threads each to be threaded to contiguous vertebrae, wherein the distal thread is threaded to the upper vertebra penetrating about 5-10 mm into the body of said upper vertebra and the proximal thread is threaded inside the pedicle and the body of the lower vertebra. This procedure is made on both intervertebral screws with screwdrivers in order to distract or contract both screws allowing to adjust or correct the intervertebral distance of the disk. The area between the distal thread and the limit stop is intended to remain within the space of the intervertebral ring. The fill hole allows the intervertebral space (intra-annular space) to be filled with a bone remodelling composition. The thread of the proximal secondary body (proximal thread) allows the screw to be secured to a vertebra that is adjacent to the vertebra that receives the distal thread.

In some embodiments, the outer diameter of the thread of the proximal secondary body (proximal thread) to have a greater diameter than the diameter of the distal thread. Thus, the distal thread passes more easily through the proximal thread installation area, without impairing the securing of the proximal thread to the bone of the vertebra and also moving the main body of the screw, by pushing said screw to thread the secondary body into the lower vertebra.

In some preferred embodiments, the limit stop may take different forms and the function thereof is to prevent the proximal secondary body from blocking the fill hole or holes during its travel. Preferably, the main body has a step which performs said function. Said step may be obtained, preferably, by a variation in the external diameter of the main body. The proximal body can therefore slide around the area with the smaller external diameter, but not through the area with the greater external diameter.

In some embodiments, the course of the fill holes is preferably radial, which minimizes the length thereof. To provide the fill function, the main body has at least two fill holes. More preferably, the course of the fill holes is diametric, with two outlets which connect opposite points of the wall of the main body. This arrangement allows the doctor who is carrying out the operation to check that there is at least one hole in the intervertebral space. To do this, the doctor must orient the screw so that the diametric direction of the hole coincides with the emission direction of the X-rays from the fluoroscope. The hole will therefore be visible using the fluoroscope.

The use of one or two screws for transpedicular access helps preserve the integrity of the annular disk and, in particular, the seal of the disk ring during surgical access of the intradiscal space, thus allowing the bone remodelling composition to be injected without causing leaks thereof before final solidification. The preservation of the seal and the immediate solidification (polymerization) make it possible to achieve an immediate fusion which until now was impossible using conventional intervertebral arthrodesis surgical techniques.

In some embodiments, a series of Nitinol Disc Cutters, varying in length and shape, are used to prepare the disc space to accommodate various anatomies or surgical situations. Each cutter is designed to debulk the nucleus pulposus and lightly abrade the endplates circumferentially up to a 3 cm diameter to create a bleeding bed for fusion.

In some embodiments, two series of cutters, followed by disc removal, should be performed. The first series of cutters are to debulk the nucleus and the second series of cutters are to prepare the endplates.

In some embodiments, the method further comprises introducing a bone remodeling composition in the void created in the disk space said composition promoting bone formation (i.e. autogenous bone and allogenic demineralized bone matrix (DBM) mixed with autologous blood). Typically, a total of 7 cc to 10 cc of grafting material will be required to fill the disc space. This step can be performed by pushing the material into the disc space and packing it by pushing the Inserter Rod through the cannula and repeating the loading process until the disc space is full, rotating the beveled tip to deliver material into the disc space in quadrants. After grafting is complete, using the 7 mm dilator to push bone graft material peripherally out of the center of the channel, and finally remove the 7 mm Dilator Sheath being careful to leave the Guide Pin in place; placing the selected Screw Implant over the Guide Pin advancing it with the long slot located near the handle facing dorsal until it contacts the vertebral bone; placing the selected implant over the Guide Pin. Advance implant and driver together over the Guide Pin and continuing advancing the Screw into the pedicle and through the above vertebral body. Advance the Screw Implant under fluoroscopic guidance until the portals of the rod are centered in the disc space. If additional graft material is desired post implant placement, prepare the material into a flowable consistency that can be delivered from a standard siringe through the screw after removing the guiding pin.

In some embodiments, at the end of the method is guiding wire and screw in the blocking cap closing skin in routine fashion and apply dressing to access site. Complete the 360° construct via posterior instrumentation with either pedicle screws or facet screw until the disc space is completely filled.

Figure 2:
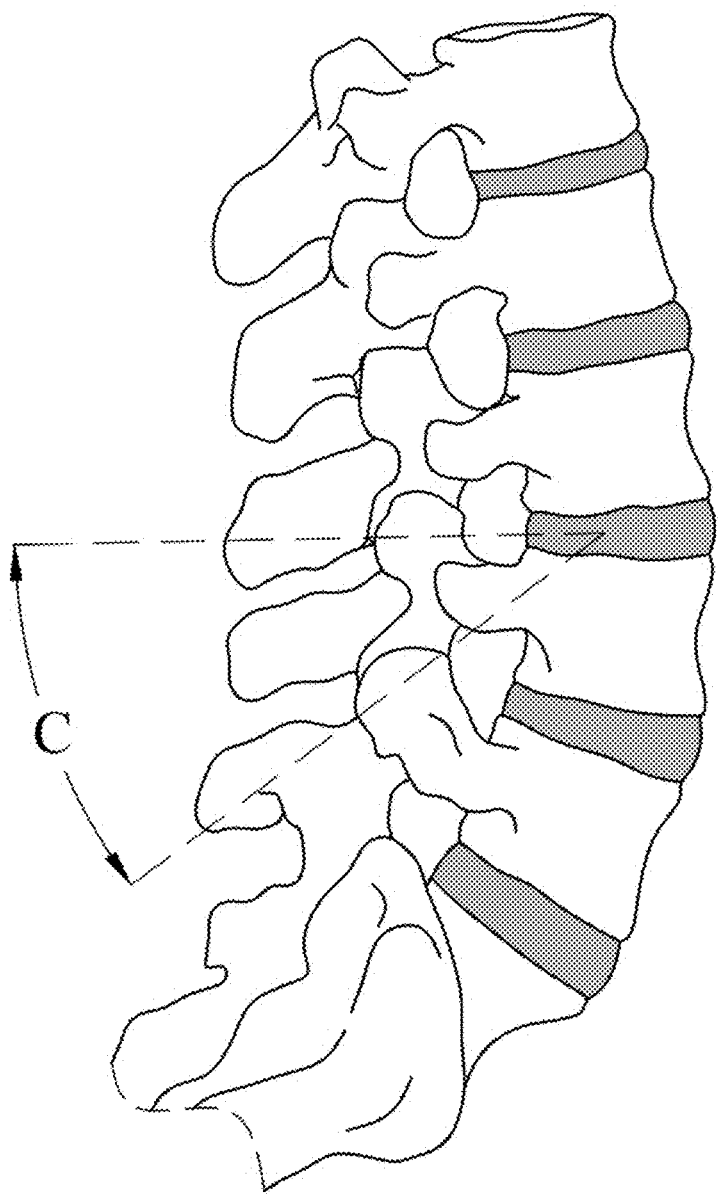
FIG. 2 is a view from an axial plane of the level to be fused of the previous figure, in which the placement trajectory of the screw has also been marked.
Figure 3:
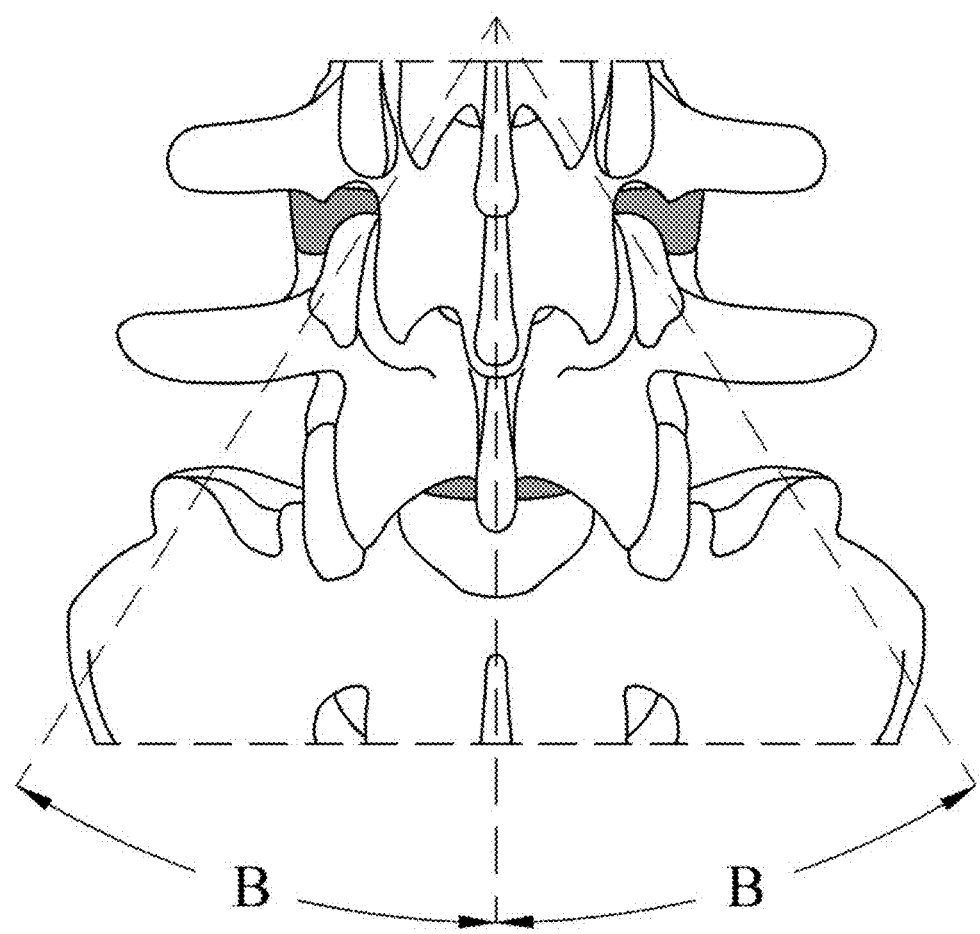
FIG. 3 is a view from a coronal plane of the spine shown in the previous figures, with the placement trajectory of two screws according to an embodiment of the present disclosure also marked.

FIGS. 1 to 3 show the preferred placement trajectory of two screws according to some embodiments of the present disclosure for fusing a vertebral level. Two screws are sufficient. The introduction thereof is transpedicular, passing through the disk space in such a way that the distal thread will be threaded in the upper vertebra and the proximal thread in the lower vertebra.

The preferred access point for percutaneous placement is situated in the pedicle, in the center of the upper articular process and approximately 1 mm below the lower edge of the transverse process of the vertebra, varying according to the specific anatomy and other factors.

The angle of introduction (defined by the value of the angles -A- (FIG. 1), -B- (FIG. 3), and -C- (FIG. 2) also varies depending on the specific anatomy of the vertebra. An optimal value for an L4-L5 fusion would be 35±5° for each of the three values (-A-, -B-, -C-), more preferably 35°.

FIGS. 4 to 11 show an example of an installation process of an embodiment of an intervertebral fusion device according to certain embodiments of the present disclosure.

For the application shown, an 11G Jamshidi-type trocar may be used for example for accessing and penetrating the pedicle and a Kissner needle as a guide for the placement of the screw. Placement is transcutaneous, bilateral and pedicular. Using fluoroscopic techniques, its passage through the disk space and penetration 5-10 mm into the body of the upper vertebra and through the lower platform of the upper vertebra can be controlled.

The process begins with ablation or nucleolisis, for example by radiofrequency, of the material inside the disk -1-. This can be carried out with a Jamshidi-type cannula -2-, as shown in FIG. 4. This technique appears viable, as it has already been applied to the ablation of metastatic posterior vertebral body osseous tumours using a bipolar device for ablation by radiofrequency. Alternatively, the material may also be removed mechanically. The cannula -2- may have been inserted by guiding, using sufficiently known percutaneous techniques. In the figure, a single cannula has been shown, but two may be inserted, one on either side. This technique has the advantage of making possible the preservation of the disk ring.

Figure 5:
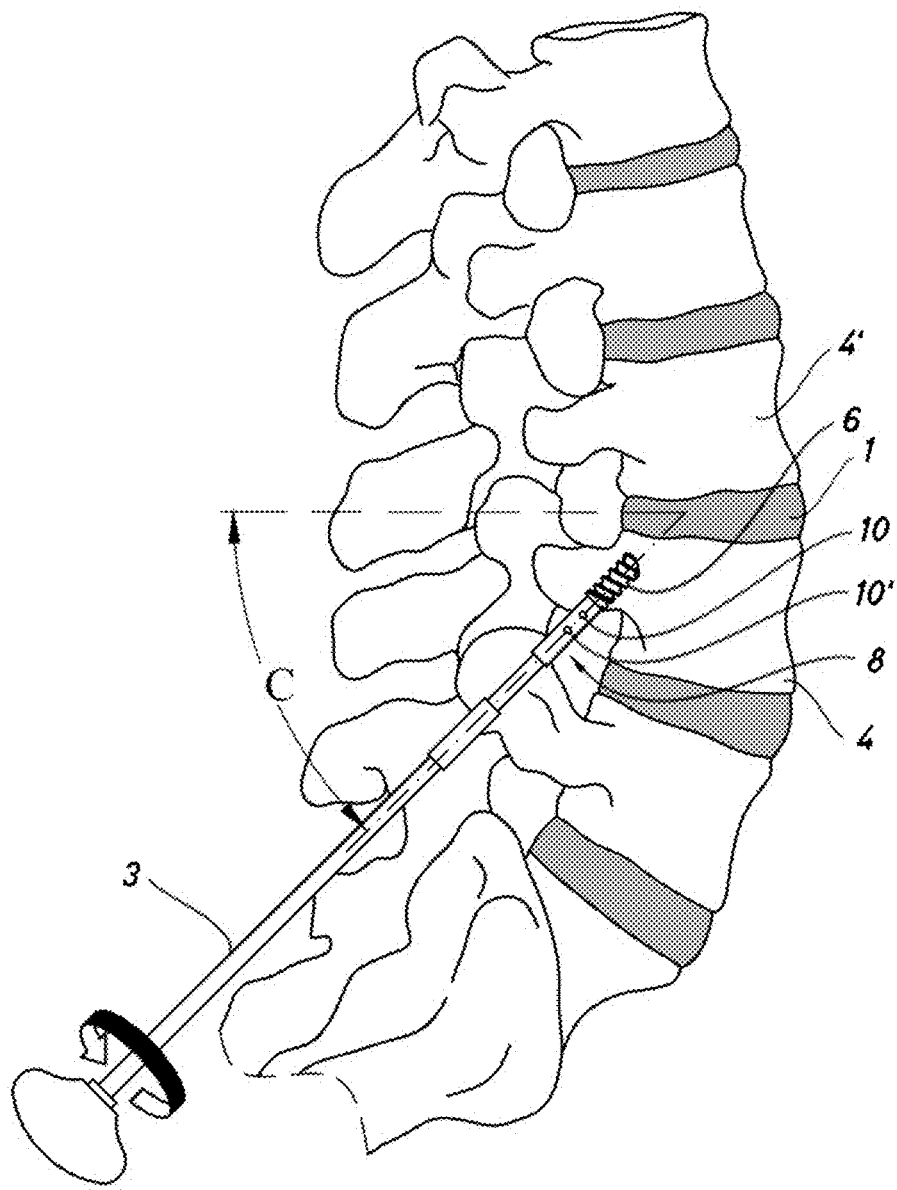
FIG. 5 shows diagrammatically a second phase of the device placement process.

Next the waste disk material produced by the nucleolisis is drawn off. To do this, a cleaning fluid is introduced at one side and removed at the other side, which draws out the waste material. To do this, two transpedicular cannulas may be used such as the cannula -2- shown in FIG. 4, one on either side of the vertebrae -4-. In FIGS. 5 and 6 an alternative technique has been shown in which two screws are introduced, said screws being threaded using the appropriate tool -3-, until the distal hole -10- of both screws is situated in the distal space and the cleaning fluid is then circulated through the two axial holes -10'- of both screws. The main body -8- of the screw enters until the distal thread -6- is threaded into the upper vertebra -4'- and the holes -10-, -10'- are in the interior disk space -1-.

Figure 7:
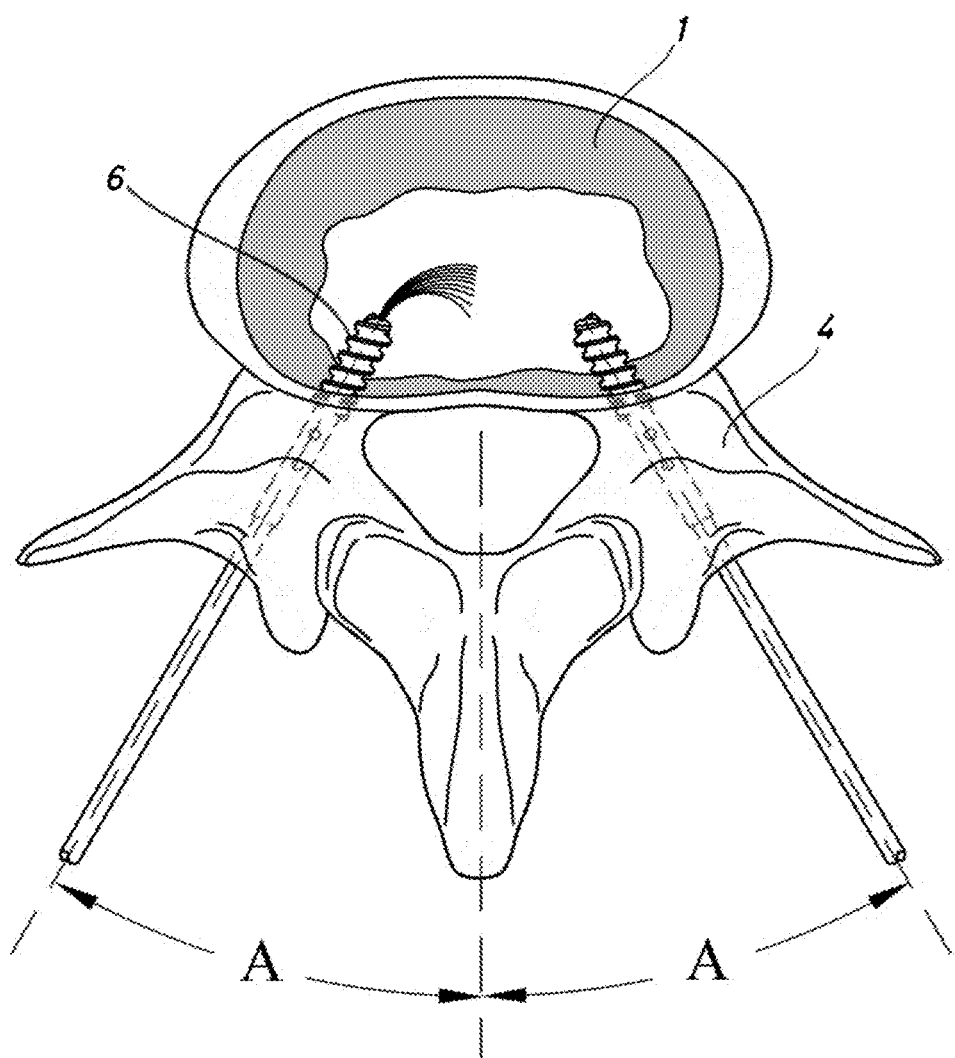
FIG. 7 shows diagrammatically a fourth phase of the device placement process.

Once the disk space has been cleaned, the vertebral platforms of the adjacent vertebrae -4-, are scraped (or stippled) (see FIG. 7). This can be done in various ways and with different tools. For example, as an alternative to the tool shown in FIG. 7, an osteotome may be used, for example the osteotome marketed under the name DFINE Midline®, or the like, to make multiple perforations in the platforms. Using this technique, new bone will grow from the platforms and will remain connected thereto.

Figure 8:
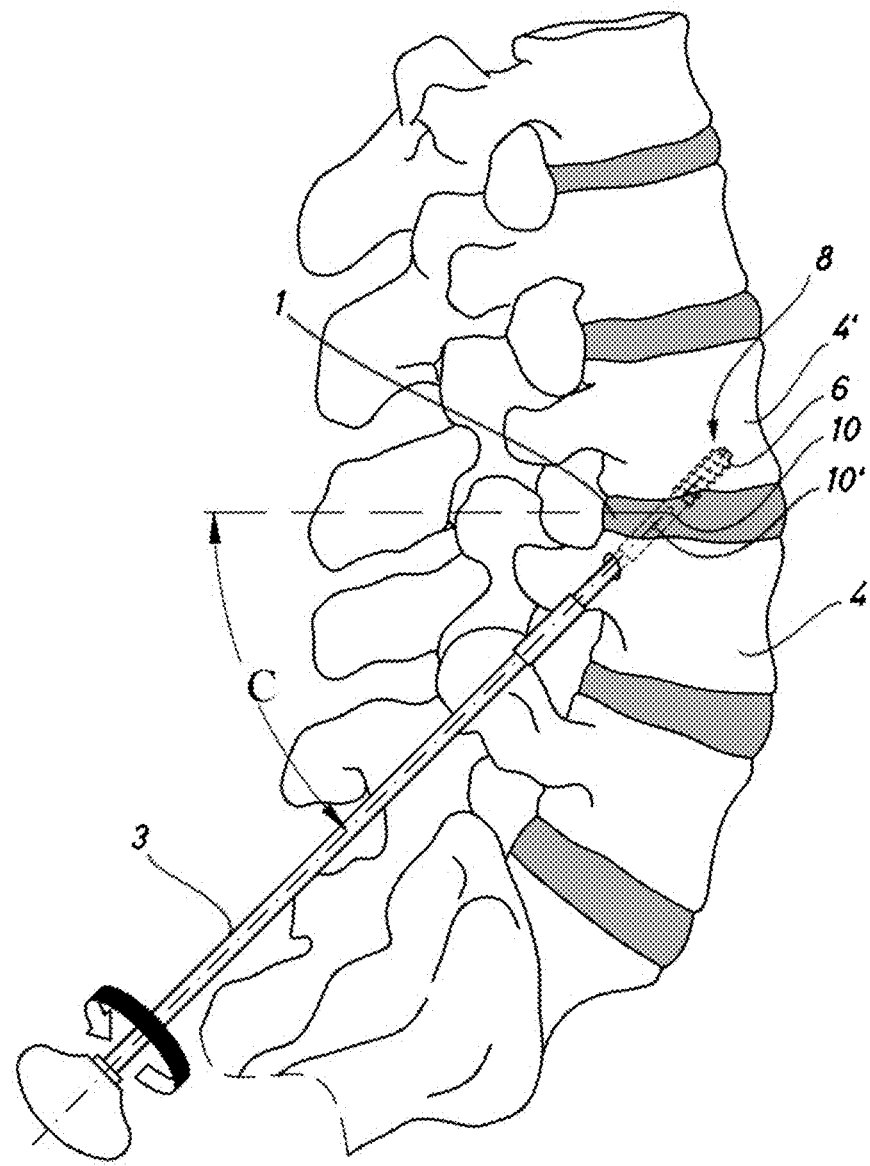
FIG. 8 shows diagrammatically a fifth phase of the device placement process.
Figure 9:
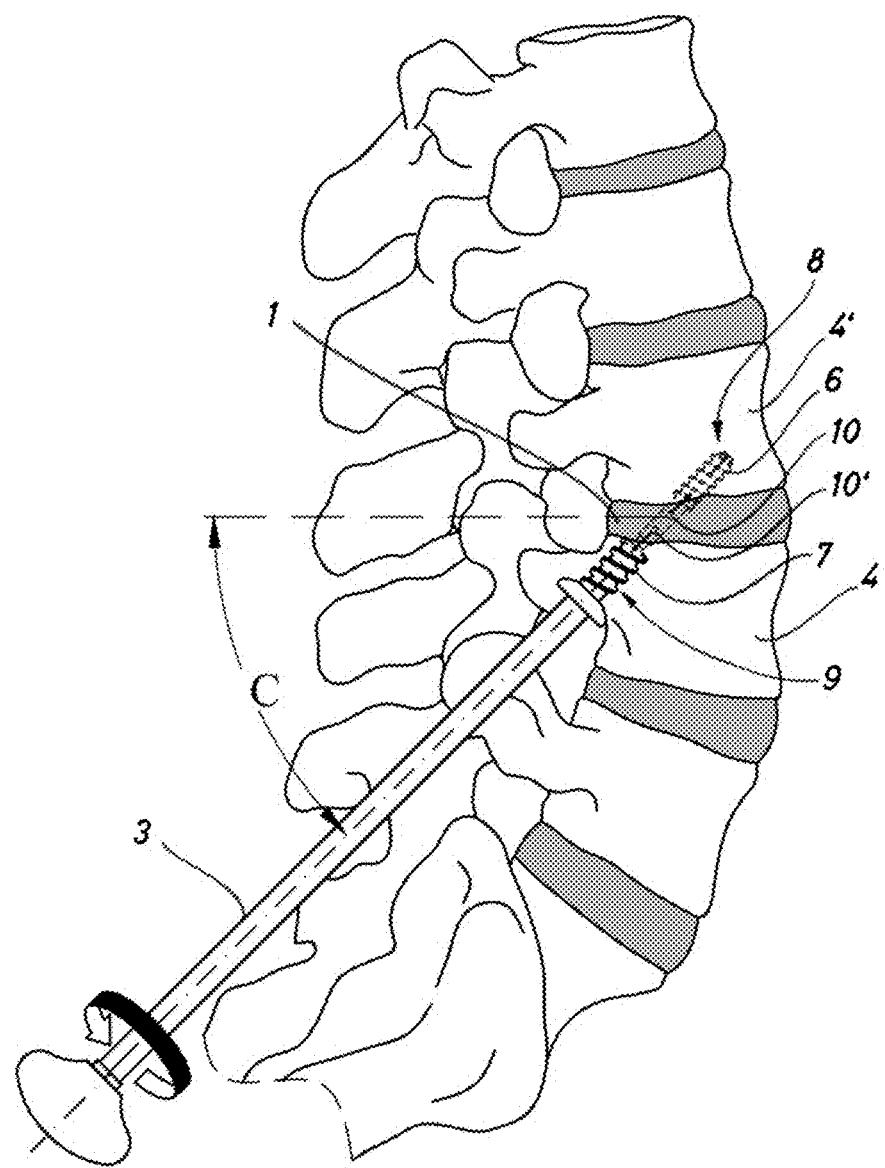
FIG. 9 shows diagrammatically a sixth phase of the device placement process.
Figure 10:
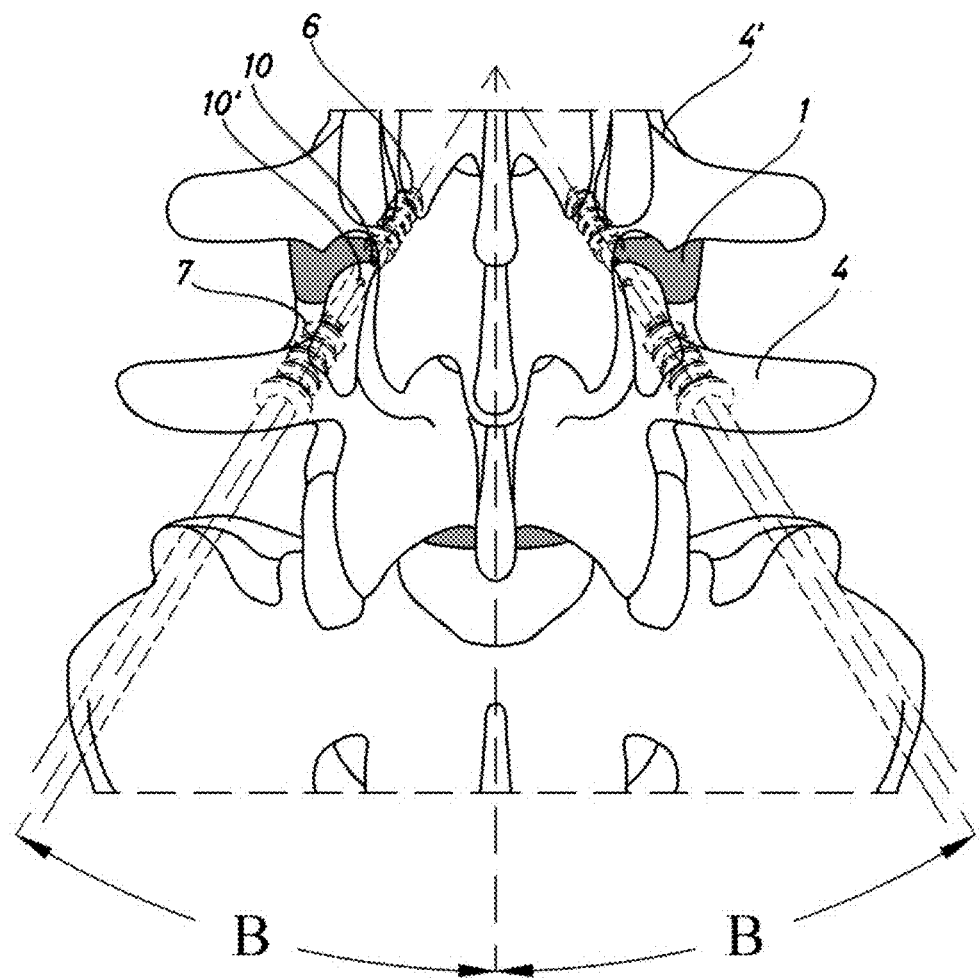
FIG. 10 shows diagrammatically a seventh phase of the device placement process.
Figure 11:
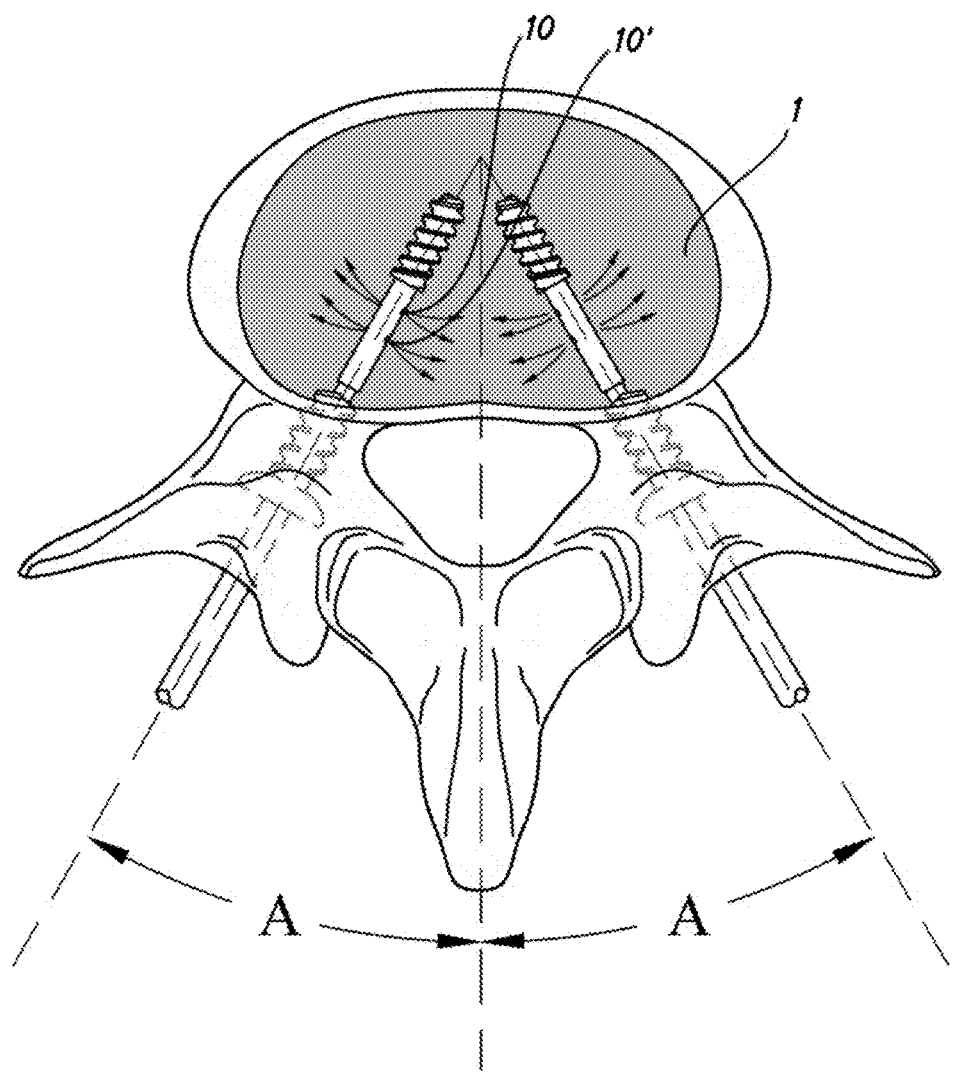
FIG. 11 shows diagrammatically an eighth phase of the device placement process.

Once the nucleus of the ring has been cleaned and the vertebral platforms have been scratched, the screw according to some embodiments of the present disclosure can be introduced up to the end of its travel (see FIGS. 8 to 10).

Initially, the main body -8- of the screw enters until the distal thread -6- is threaded into the upper vertebra -4'- and the holes -10-, -10'- are in the interior disk space -1-. The bilateral placement process, with two screws, allows some correction of any vertebral deviations.

Next, the proximal body -9- of the screw is threaded inside the pedicle and the body of the lower vertebra -4- until reaching the limit stop (see FIG. 9). Once the limit stop has been reached, it is possible to continue threading the proximal thread -7- against the limit stop. This creates a distraction which produces slight intervertebral lordosis. This effect is recommended, as most patients who require fusion have lost lordosis. The use of this over-threading also allows vertebral distractions to be corrected.

Once the screws have been put in place, the Kissner-type guide needle (not shown in the figures) can be removed and the void created in the disk space can be filled with a bone remodelling composition.

To produce the bone regeneration composition according to some embodiments of the present disclosure any type of polymerisable bone cement can be used. Polymerization allows the cured bone cement to be introduced in a liquid or semi-liquid state with immediate hardening of the bone cement inside the intervertebral disk.

Before the end of polymerization the composition is introduced into the disk void that has been produced (see FIG. 10) while checking that said composition does not come out of the disk space limited and contained by the disk ring and waiting for a few minutes until polymerization is complete. The composition comes out through the outlet fill holes -10-, -10'-.

Figure 12:
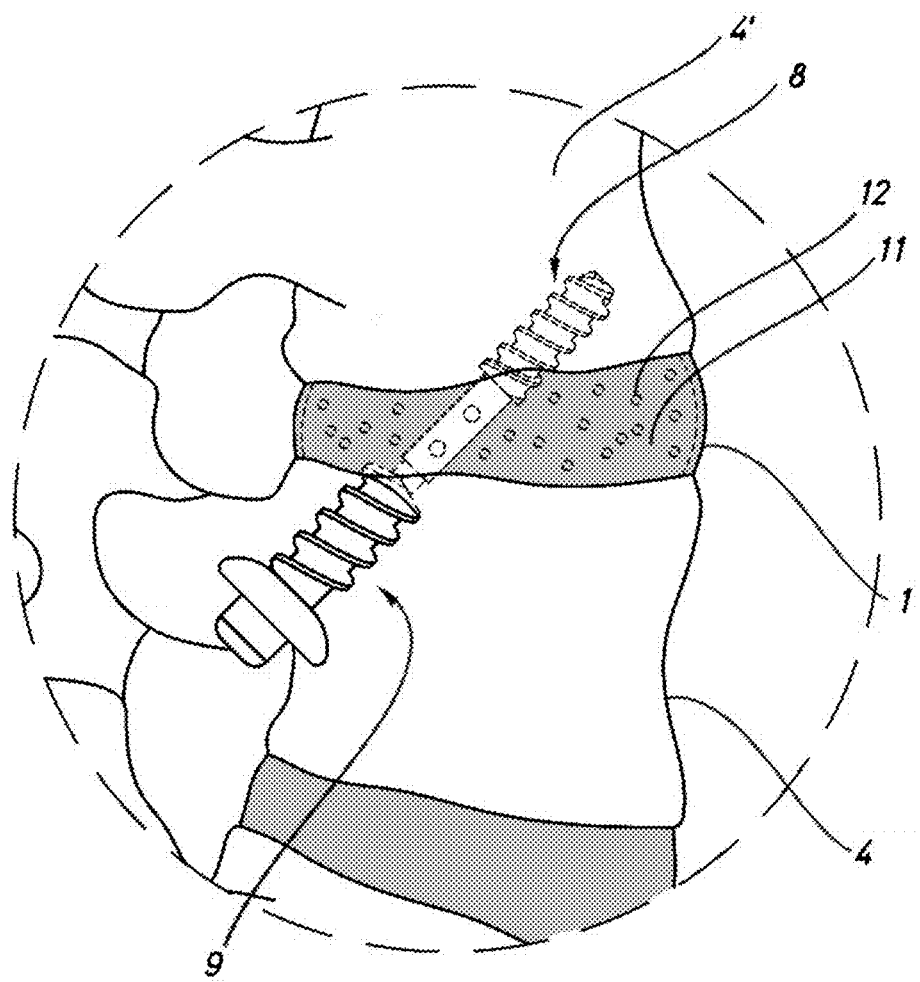
FIG. 12 shows from a lateral viewpoint a device according to an embodiment of the present disclosure already in place and prepared for the fusion of a vertebral level.

Once hardened, the composition introduced inside the disk -1- produces a bed -11- with numerous pores -12- in which bone will grow from the damaged areas of the platforms of the upper -4'- and lower -4- vertebrae (see FIG. 12). Growth is maximized by the presence of oxygen and osteogenic growth factors inside the disk space and enhanced by the availability of calcium phosphate, preferably hydroxyapatite.

Although the present disclosure relates to certain preferred embodiments, said embodiments should not be considered as limiting the invention, which will be defined by the widest interpretation of the following claims.

Example 1: 84-Year-Old Male Patient Diagnosed with Spondylolisthesis (I Degree)

The technique described hereinabove was performed in an outpatient surgical center with local anesthesia.

In terms of the patient's preoperative examination, radiographic images of the affected spine in two projections, as well as functional MRI images were performed. It was ensured that the patient was in the proper position. The installation of the screws included the phases of cleaning the disk space, scraping, and the transpedicular installation of the screws; as necessary, correction of the relative position of the vertebrae was accomplished by threading the proximal thread against the limit stop and injecting the bone remodelling composition into the intervertebral space through the axial hole and the fill hole. To facilitate bone formation from the vertebrae, the vertebral platforms were scraped with a flexible or bendable osteotome, before introducing the bone remodelling composition.

Postoperative course was smooth. Postoperative small wound healed by primary intention, and the stitches were removed on the 7th day.

As a result of the foregoing procedure, the continued mobility of the spine with the restoration of the spinal canal configuration was ensured and provided early social rehabilitation of the patient with an increase in the quality of his life.

What is claimed is:

1. A method for instant lumbar spine fusion between two vertebrae in a patient in need thereof comprising:
   a) establishing under X-ray fluoroscopy the location of the transpedicular notch of the next lower vertebra in caudal direction;
   b) making a percutaneous incision of about 5-10 mm approximately 5 cm off of midland caudal to said transpedicular notch;
   c) inserting a cannulated guide following an anteroposterior (AP) trajectory of [C] between 18 degrees and 25 degrees and in a lateral trajectory of [A or B] between 35 degrees and 50 degrees;
   d) drilling a transpedicular approach from the pedicle of the lower vertebra to the anterior part of the vertebral body of the vertebrae above the disc to be treated;
   e) inserting a working cannula through the previously drilled approach reaching the intervertebral disk;
   f) cleaning and scrapping the intervertebral disk space;
   g) inserting transpedicularly at least one intervertebral stabilizing screw, said screw comprising two threads each to be threaded to contiguous vertebrae, wherein the distal thread is threaded to the upper vertebra penetrating about 5-10 mm into the body of said upper vertebra and the proximal thread is threaded inside the pedicle and the body of the lower vertebra; and
   h) acting on both intervertebral screws with screwdrivers in order to distract or contract both screws allowing to adjust or correct the intervertebral distance of the disk;
   wherein said method is performed on an outpatient basis using local anesthesia and wherein each of (b) through (h) is followed by active or real-time fluoroscopy.

2. A method for instant lumbar spine fusion according to claim 1, wherein the percutaneous incision of (b) is of about 8 mm.

3. A method for instant lumbar spine fusion according to claim 1, wherein after (h), the method further comprises introducing a bone remodeling composition in a void created in the disk space, said remodeling composition promoting bone formation.

4. A method for instant lumbar spine fusion according to claim 3, wherein the bone remodeling composition comprises autogenous bone and allogenic demineralized bone matrix (DBM) mixed with autologous blood mixed with calcium phosphate.

5. A method for instant lumbar spine fusion according to claim 4, wherein the bone remodeling composition further comprises a compound selected from the group consisting of poly(methyl methacrylate) (PMMA), bisphenol A-glycidyl methacrylate (bis-GMA) and poly(lactic-co-glycolic acid) (PLGA).

6. A method for instant lumbar spine fusion according to claim 5, wherein the bone remodeling composition comprises PMMA or PLGA.

7. A method for instant lumbar spine fusion according to claim 3, wherein the bone remodeling composition comprises osteogenic factors selected from the group consisting of whole blood, blood-derived growth factors and osteogenic stem cells.

8. A method for instant lumbar spine fusion according to claim 7, wherein the osteogenic factors are blood-derived growth factors.

9. A method for instant lumbar spine fusion according to claim 3, wherein the volume of the bone remodeling composition is between 7 cc and 10 cc.

10. A method for instant lumbar spine fusion according to claim 1, wherein the patient in need thereof is a patient requiring fusion to treat pseudoarthrosis (unsuccessful previous fusion) spinal stenosis, spondylolisthesis (Grade 1 or 2 if single-level; Grade 1 if two-level), or degenerative disc disease as defined as back pain of discogenic origin with degeneration of the disc confirmed by history and radiographic studies.

11. A method for instant lumbar spine fusion according to claim 1, wherein a series of Nitinol Disc Cutters, varying in length and shape, are used to prepare the disc space to accommodate various anatomies or surgical situations.

12. A method for instant lumbar spine fusion according to claim 1, wherein the calcium phosphate provider is hydroxyapatite, brushite or tricalcium phosphate.

13. A method for instant lumbar spine fusion according to claim 12, wherein the calcium phosphate provider is hydroxyapatite.

14. A method for instant lumbar spine fusion according to claim 1, wherein the external diameter of the proximal thread is greater than the diameter of the distal thread of the intervertebral stabilizing screw.

15. A method for instant lumbar spine fusion according to claim 1, wherein the intervertebral stabilizing screw of comprises at least two fill holes.

\* \* \* \* \*